United States Patent [19]

Wilson et al.

[11] Patent Number: 5,383,932
[45] Date of Patent: Jan. 24, 1995

[54] ABSORBABLE MEDULLARY PLUG

[75] Inventors: Stephen Wilson, Raynham; Laurel Rogers, North Attleboro, both of Mass.; Allan Ritchie, Lymington, England

[73] Assignee: Johnson & Johnson Professional, Inc., Raynham, Mass.

[21] Appl. No.: 53,833

[22] Filed: Apr. 27, 1993

[51] Int. Cl.6 ................................ A61F 2/28
[52] U.S. Cl. ............................... 623/16; 606/95
[58] Field of Search ..................... 623/16, 23, 17; 606/224, 92, 95

[56] References Cited

U.S. PATENT DOCUMENTS

| 4,293,962 | 10/1981 | Fuson | 623/16 |
| 4,344,190 | 8/1982 | Lee et al. | 623/16 |
| 4,932,962 | 6/1990 | Yoon et al. | 606/224 |
| 4,981,149 | 1/1991 | Yoon et al. | 606/224 X |
| 5,074,874 | 12/1991 | Yoon et al. | 606/224 |
| 5,092,891 | 3/1992 | Kummer et al. | 623/16 |
| 5,092,892 | 3/1992 | Ashby | 623/16 |

FOREIGN PATENT DOCUMENTS 2017503 10/1979 United Kingdom ............ 623/16

Primary Examiner—Randall L. Green
Assistant Examiner—Elizabeth M. Burke

[57] ABSTRACT

A bone plug for intramedullary insertion into the canal of a bone to restrict the bypass of cement during implant surgery is described. The bone plug is made of a bioabsorbable material and has a tapered central body providing the primary support for the plug. A plurality of radially extending disc-like fins extend from the body at spaced locations. The taper provides the distal fin with a greater degree of flexibility due to the long cantilever, thus permitting an ease of insertion into the intramedullary canal while the larger diameter body and shorter proximal fins lend structural stiffness to resist the migration of the device.

20 Claims, 3 Drawing Sheets

ABSORBABLE MEDULLARY PLUG

FIELD OF THE INVENTION

The present invention relates to orthopaedic products and in particular plugs for long bone canals which restrict the flow of cement during prosthesis implantation.

BACKGROUND

During implant surgery and in particular the implantation of a hip prosthesis, it has long been known to cement the prosthesis to the bone. In order to cement the prosthesis to the bone, the bone canal is broached or reamed to the desired shape to match the shape of the prosthesis anchoring portion. An anchoring portion of the prosthesis is then inserted, for example into the broached femoral bone to replace the natural ball portion of the hip bone.

In order to fix the anchoring portion to the long bone, it has been known to use cements such as polymethylmethacrylate (PMMA) which is inserted into the bone canal and packed upon the prosthesis prior to insertion of the prosthesis. These cements such as PMMA then anchor the anchoring portion of the prosthesis to the bone material.

In order to provide for a secure joint between the prosthesis and bone at the cement interface, it is desired to have the cement completely surround the prosthesis in the interstices between the prosthesis and the bone material. However, the insertion forces required to insert the implant often drive the cement substance down into the intramedullary canal and away from the fixation site. In this way, voids are formed in the cement mantle which later become stress points leading to early failure of the devices.

In order to address this concern, intramedullary devices such as plugs have been developed by manufacturers of implants in order to restrict the flow of the bone cement further into the intramedullary canal than is desired. Thus, when the implant is forced into the broached portion of the intramedullary canal the tendency of the thick bone cement to flow down the canal is prevented by the presence of blockage in the form of an intramedullary bone plug.

For example U.S. Pat. No. 4,245,359 shows a plug made of a plastic material which acts as a cement barrier for openings produced by operative procedures. The plug is clamped between the side walls of the opening by means of elastic flanges which prevent bone cement from escaping downward upon insertion of a stem portion. U.S. Pat. No. 4,293,962 shows a device for plugging the medullary canal in joint replacement surgery technique. The plug prevents the cement used for fixation from extending beyond the point where it is useful. The device is comprised of a tapered cylindrical plug which is threadedly engaged to a flexible insertion shaft. The plug is lodged in the appropriate place in the canal and the plug is made of a bio-compatible material. U.S. Pat. No. 4,302,855 discloses a bone plug for use in the intramedullary canal of a bone. The bone plug includes a resilient body of medical grade material. The body has a smooth, blunt, rounded nose, a mid point joined to the nose and having a toroidal shape and upper, open-ended portion joined to the mid portion and defining a recess. The upper, open-ended portion is generally frusto-conical in nature and further defines a plurality of circumferential spaced petal-like elements.

U.S. Pat. No. 4,344,190 shows a pressure fit plug which prevents cement from penetrating down the canal. The plug is described as being capable of being made of biodegradeable material so that in time is dissolves away.

U.S. Pat. No. 4,447,915 describes a medullary canal plug which is formed of a deformable and expandable outer body having a jacket formed of a number of segments in a conical expansion body which is pulled into the outer body in order to expand the outer body.

U.S. Pat. No. 4,697,584 describes an inflatable intramedullary plug used to plug the open end of intramedullary bone canal. And U.S. Pat. No. 5,092,891 describes a cement plug for sealing the medullary canal of a bone. The plug is composed of biocompatible plastic and is comprised of a tubular body which is slit axially having an obturator plate located at the upper end of the body and a tapered conical plug that can be advanced through the lower end of the body into the interior of the body. This causes expansion and engagement of the plug within the intramedullary canal.

SUMMARY OF THE INVENTION

The present invention provides a new absorbable bone plug or cement restrictor which is absorbable. The restrictor has substantially equivalent insertion forces to prior known restrictor devices however, resists migration to a greater degree. The absorbable intramedullary bone plug comprises a tapered longitudinal body which has extending therefrom a plurality of longitudinally spaced fins. Each of these fins provides a continuous outer edge and may be substantially disc shaped in the transverse plane, that is, transverse to the longitudinal axis of the body.

The plug is formed of an absorbable material such as poly(p-dioxanone) and has been found to be more flexible than absorbable plugs of other prior designs. The body is provided with a taper which ranges from approximately 2° to approximately 20° and is preferrably 10° total. That is the body has a 10° taper (5° along each side to the center axis) and is frustoconical in nature. The body may terminate at a bottom fin or may extend slightly beyond the bottom fin.

In smaller sizes the plug has a cyclindrical upper portion and then tapers, sometimes at a more substantial degree i.e. 15° (7.5° to the longitudinal axis). This provides upper strength to the bone plug while still permitting flexibility to lower spaced fins. These fins preferrably are disc shaped and taper from a root which is adjacent the body portion to an outer circumferencial perimeter. The fins taper from approximately 2° to approximately 10° to the central plane of the fin and preferrably taper at approximately 5°. The plug has an opening defined at a proximal end which is threaded to receive an inserter. This threaded opening mates with the threaded end of the inserter rod for positioning within the bone canal.

BRIEF DESCRIPTION OF THE DRAWINGS

The invention will now be described with reference to the accompanying drawings wherein.

DESCRIPTION OF THE PREFERRED EMBODIMENTS

Figure 1:
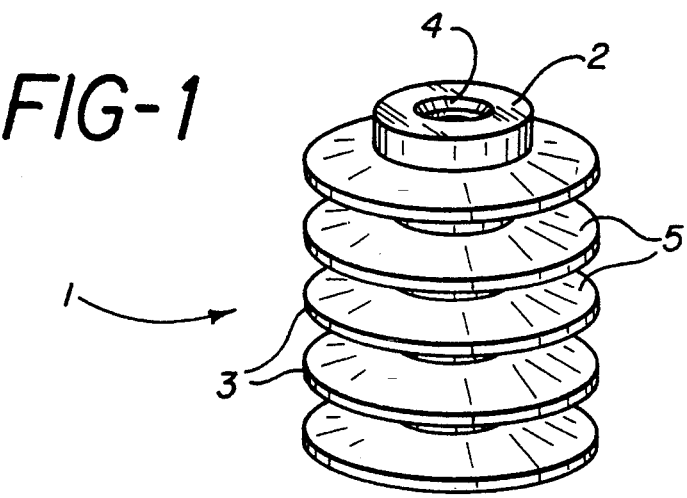
FIG. 1 is a perspective front view of the bone plug of the present invention.

Referring now to FIG. 1, there is shown a plug 1 having a main central body 2 and plurality of fins 3 extending therefrom. The plug has an inserter opening 4 formed in an upper surface thereof.

Figure 2:
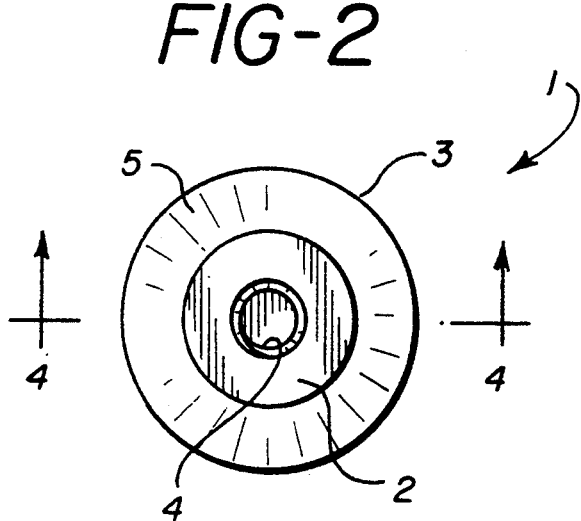
FIG. 2 is a top plan view of the plug of the present invention.
Figure 3:
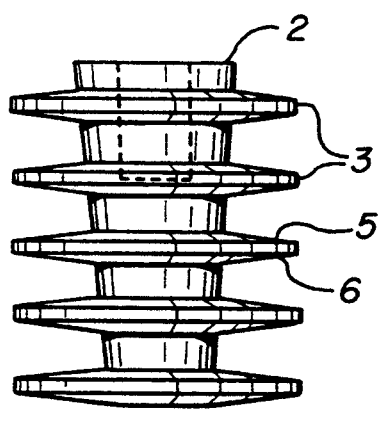
FIG. 3 is a front elevation view of the plug of the present invention.

FIG. 2 shows a top plan view of the plug of FIG. 1, showing the extension of the fin 3 beyond the body portion 2. Typically the fin extends from 0.094 to 0.183 inches beyond the upper terminus of the body. The first fin (top fin) typically starts 0.038 inches below the top of the body and ranges between 0.045 and 0.028 inches depending on size. This measurement is taken from the top surface of the body to the top surface of the fin at its outer most terminus. The diameter of the top portion of the body for example may be 0.66 inches for a mid-size bone plug. As seen in FIG. 3 the remaining fins extend to the same diameter as the top fin, however, have a longer cantilever portion due to the taper of the body 2. The remaining fins are typically set at a 0.156 inch pitch and have a thickness at their outer most end of 0.025 inches. The body 2 tapers at a 10° rate. That is, the body tapers along each side at 5° to the longitudinal center axis for a total conical shape of 10°. The upper fin surface 5 and lower fin surface 6 taper toward the outer edge of the fin at typically a 10° angle to one another. That is, each tapers with respect to a center line of the fin at 5° for a total taper of 10° from a wide portion at the body interface to a narrow portion extending from the body.

A standard medium to large size cement restrictor is shown in the figures, however, the very small sizes i.e. approximately 0.58 inches and 0.50 inches in total diameter have a cylindrical upper portion to the body and the taper is formed only along the lower portion. The cylindrical portion extends between the top two fins and then the body tapers along its final length typically having three fins in the portion of the body which is tapered. Taper remains at typically a 10° total angle from side to side but the cylindrical start to the body shape prevents the lower most fin from being rooted in too narrow a body portion.

Figure 4:
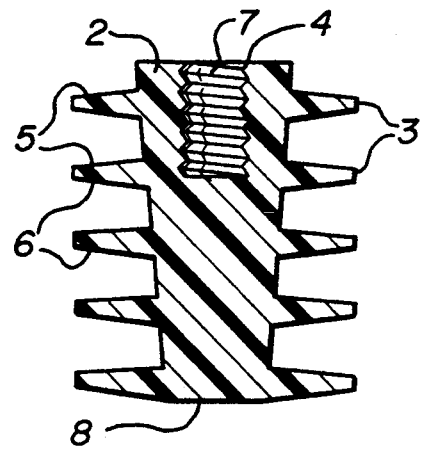
FIG. 4 is a cross-sectional view taken along lines 4—4 of FIG. 2.

Furthermore, it is preferred to have the distal tip of the body form a smooth surface with the bottom surface of the lower most fin as shown in FIG. 4.

Formed within the upper portion of the body is a threaded opening 4 having threads 7 therein. The threads typically are 8-32 threads which mate with a comparable inserter to be described below. The threaded opening extends within the body to a depth of typically 0.25 inches to provide sufficient support for the inserter.

Alternatively the distal end of the bone plug may be chamferred at approximately a 45° angle and a 0.025 inch depth in order to smooth the corner of the lead edge of the plug body. This is preferred in an alternative embodiment (not shown) having the distal end of the body extending beyond the lower most fin.

The plug is made by injection molding poly(p-dioxanone) commonly referred to as PDS. A thorough account of the process for making PDS is given in U.S. Pat. No. 4,052,988 issued Oct. 11, 1977, which is incorporated herein by reference. PDS is absorbable providing one of the unique features of the invention. The plug itself may be machined either in total formation or as a subsequent process to the injection molding process. For example although it is preferred to mold threads 7 directly, the threads 7 may be machined into the opening 4 after formation of the body blank is made by injection molding.

Tests were run to compare the cement restrictor of the present invention to two commercially available restrictors. An absorbable medullary plug of the size 14/15 mm having an overall diameter of 0.66 inches and an initial fin that extended 0.156 inches beyond the body which body tapered at a 5° angle with respect to the central axis of the plug (10° overall taper) was compared to a DePuy size 5 (18.25 mm) femoral cement restrictor available from DePuy, Warsaw, Indiana (a Division of Boehringer Mannheim Corporation) and a Richards 25 mm OD Buck Femoral Cement Restrictor available from Smith & Nephew Richards, Inc., Memphis, Tenn.

The restrictors were inserted using a hydraulic testing machine. The restrictors were loaded axially as they were inserted into tubes having a tapered lead-in and a constant inner diameter. Each cement restrictor was inserted 30 mm into the tube at a rate of 50 mm per second, the insertion force data is then tabulated. From a static state, the cement restrictor is again loaded axially and inserted in an additional 30 mm at a rate of 50 mm per second, producing migration force. After a one second pause the cement restrictor is withdrawn from the tube at a rate of 50 mm per second. The tubes were Celcon ® tubes with inner diameters of 14.3 mm and 15.1 mm. The Richards cement restrictor is sized according to the OD of the largest fin. The cement restrictor consists of two circumferential fins, the second smaller fin is located approximately 4 mm distally along the core. The diameter of the second fin for the small and large cement restrictors available from Richards are 13 mm and 18.5 mm respectively. The test resulted in the following insertion and migration force results.

| PLUG TYPE | 14.3 mm Insertion avg (N) | 14.3 mm Migration avg (N) | 15.1 mm Insertion avg (N) | 15.1 mm Migration avg (N) |
| --- | --- | --- | --- | --- |
| DePuy | 321.9 | 178.5 | 471.9 | 171.6 |
| Richards | 234.9 | 87.8 | 206.7 | 84.6 |
| Invention | 407 | 273.3 | 443.9 | 206.9 |

The dimensions and the results are in Newtons. As can be seen from the tabulated results, the insertion force of the device of the present invention was approximately equivalent to the other test specimens. However, the resistance to migration force was significantly greater than the specimen of the present invention, it is believed that this occurs due to the overall stiffness of the proximal fins of the present restrictor and their resistance to migration pressures and the overall flexibility of the distal fins which produce a reduction in insertion force for comparable restrictors.

Figure 5:
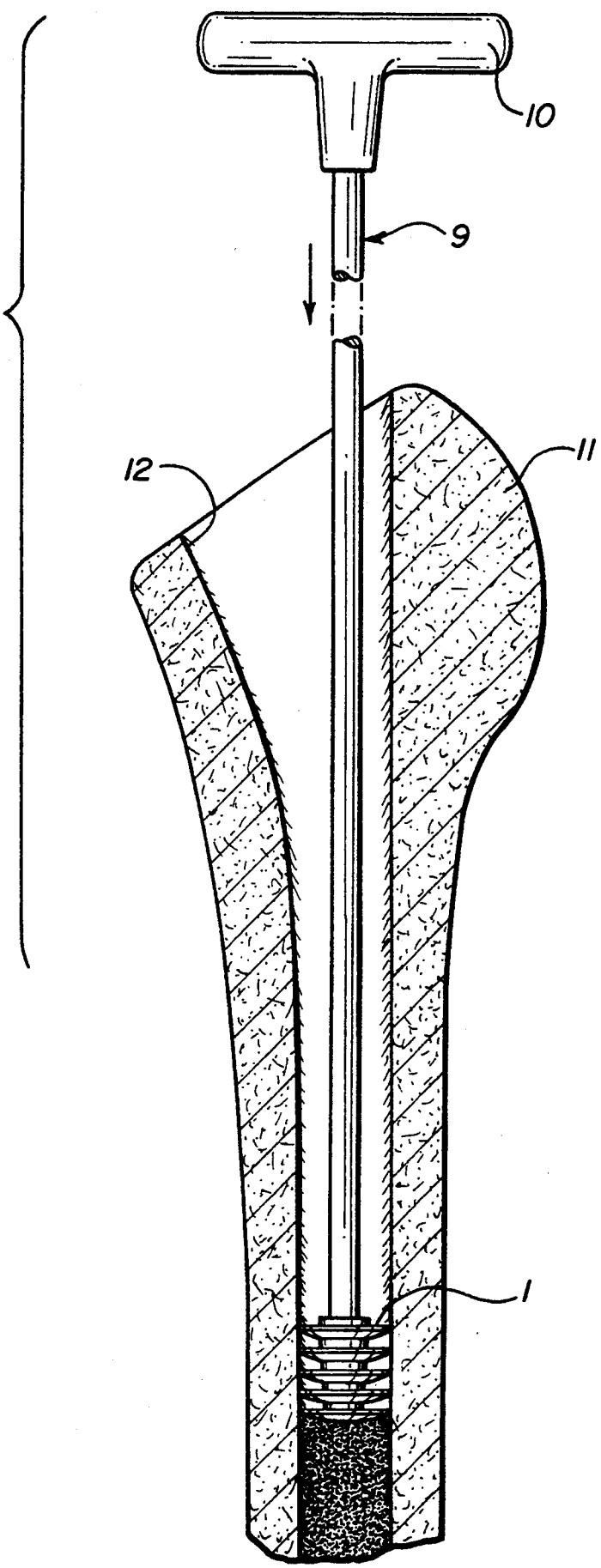
FIG. 5 is a cross-sectional view of a bone showing insertion of the bone plug of the present invention; and, FIG. 6 is a cross-sectional view of a bone having a phantom implant and cement mantle in place within the intramedullary canal.
Figure 6:
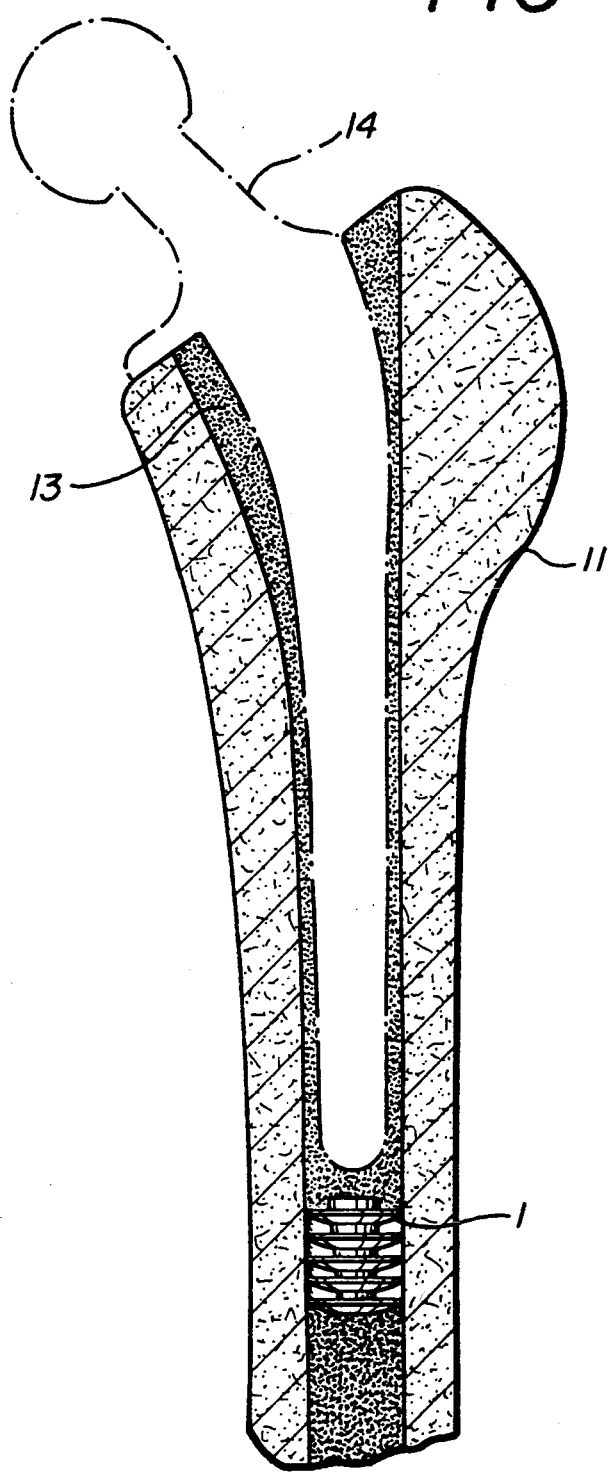

In use, the plug is attached to the threaded end of an inserter 9 having a handle 10 (FIG. 5). Once the bone 11 has been prepared by reaming the canal 12 for receipt of the prosthesis the plug is inserted, using the inserter, into the canal to the desired depth for restriction of flow of cement (FIG.6). Common operative technique is then used to implant the prosthesis using a typical bone cement. The cement 13 forms a mantle around the prosthesis 14 which is consistent due to the flow resistance provided by the plug.

Uniquely the tapered body structure of the plug permits the lower fins (i.e. the fins at the distal end) to flex more than the fins at the proximal end of the plug. Due to the longer cantilever, although thicker due to the taper, the distal fins will flex more than the proximal fins. Thus when received within a tapering canal the distal fins will permit flexing and therefore further insertion without fin breakage. If for example the body had a consistent cylindrical shape each of the fins would have approximately the same flexural resistance. As the plug body is inserted into the tapering intramedullary canal, however, the lower fins would receive a greater amount of this force and therefore would be more likely to fracture during insertion. Also, the lower fins would provide greater transverse pressures on the bone creating the potential for complication. The present invention eliminates this problem by having longer cantilevers to the distal fins, making them more flexible.

The plug being made of PDS material provides for the bioabsorption of the plug itself after the implant is fixed in place. The body material is absorbed over an extended period of time thus relieving the stresses on both the cement and the adjacent bone provided by the presence of the bone plug. This eliminates one of the drawbacks of prior known bone plugs. It is easily seen that although the bone plug need be present when the bone cement is in soft state, once the bone cement has cured or hardened, the need for the bone plug is no longer present and its removal by bioabsorption is a greatly desirable feature.

Furthermore, the fins of the present invention are continuous about their outer circumferential extent. That is, rather than being formed as a plurality of fins at each level or in a petal shape as shown in the prior art, the present fins provide a consistent and more assured resistance to the bypass cement material. This sealing feature is provided without the loss of the ease of insertion which is provided by the additional flexibility created by the taper of the body.

What is claimed is:

1. An absorbable intramedullary bone plug for restricting cement flow in prosthesis implant surgery comprising a tapered longitudinal body having extending from the tapered longitudinal body a plurality of longitudinally spaced fins, each fin providing a continuous outer edge, said fins extending to approximately equal final diameters.

2. An absorbable bone plug according to claim 1 wherein the plug is made from poly(p-dioxanone).

3. The absorbable bone plug according to claim 1 wherein the body defines a central longitudinal axis and tapers from approximately 2° to approximately 20° with respect to the central longitudinal axis of the body.

4. The absorbable bone plug according to claim 3 wherein the body tapers at approximately 5° with respect to the longitudinal axis of the body.

5. The absorbable bone plug according to claim 1 wherein the fins are disc shaped and taper from a root adjacent the body to an outer circumferential perimeter.

6. The absorbable bone plug according to claim 5 wherein the fins taper at approximately 2° to 10° to a central plane of the fin.

7. The absorbable bone plug according to claim 5 wherein the fins taper at approximately 5° to a central plane of the fin.

8. The absorbable bone plug according to claim 6 wherein the central plane runs perpendicular to a central axis of the body.

9. The absorbable bone plug according to claim 1 wherein an opening is defined in a proximal end of the body of the bone plug for receipt of an inserter.

10. The absorbable bone plug according to claim 9 wherein the opening defines a threaded portion for threadably mating with a distal end of an inserter for insertion into a bone canal.

11. An absorbable intramedullary bone plug comprising a central core having a first proximal portion which is substantially cylindrical in shape about a central longitudinal axis and a second distal portion which is tapered in the longitudinal direction said core having extending from said second portion a plurality of longitudinally spaced fins, each fin providing a continuous outer edge and said fins extending to approximately equal diameters.

12. An absorbable bone plug according to claim 11 wherein the plug is made from poly(p-dioxanone).

13. The absorbable bone plug according to claim 11 wherein the distal portion tapers from approximately 2° to approximately 20° with respect to the central longitudinal axis of the core.

14. The absorbable bone plug according to claim 11 wherein the central core tapers at approximately 7.5° with respect to the longitudinal axis of the core.

15. The absorbable bone plug according to claim 11 wherein the fins are disc shaped and taper from a root adjacent the core to an outer circumferential perimeter.

16. The absorbable bone plug according to claim 15 wherein the fins taper at approximately 2° to 10° to a central plane of the fin.

17. The absorbable bone plug according to claim 15 wherein the fins taper at approximately 5° to a central plane of the fin.

18. The absorbable bone plug according to claim 16 wherein the central plane runs perpendicular to a central axis of the core.

19. The absorbable bone plug according to claim 11 wherein an opening is defined at a proximal end of the core of the bone plug for receipt of an inserter.

20. The absorbable bone plug according to claim 19 wherein the opening defines a threaded portion for threadably mating with a distal end of an inserter for insertion into a bone canal.

* * * * *